(12) United States Patent
Koehler et al.

(10) Patent No.: US 10,912,532 B2
(45) Date of Patent: Feb. 9, 2021

(54) SCATTER CORRECTION FOR DARK FIELD IMAGING

(71) Applicant: KONINKLIJKE PHILIPS N.V., Eindhoven (NL)

(72) Inventors: Thomas Koehler, Norderstedt (DE); Hanns-Ingo Maack, Norderstedt (DE); Andriy Yaroshenko, Garching (DE); Klaus Juergen Engel, Veldhoven (NL); Bernd Menser, Hauset (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/633,719

(22) PCT Filed: Jul. 26, 2018

(86) PCT No.: PCT/EP2018/070295
§ 371 (c)(1),
(2) Date: Jan. 24, 2020

(87) PCT Pub. No.: WO2019/020748
PCT Pub. Date: Jan. 31, 2019

(65) Prior Publication Data
US 2020/0205765 A1 Jul. 2, 2020

(30) Foreign Application Priority Data
Jul. 26, 2017 (EP) ..................................... 17183174

(51) Int. Cl.
*A61B 6/00* (2006.01)
*G06T 5/00* (2006.01)

(52) U.S. Cl.
CPC ............ *A61B 6/5282* (2013.01); *A61B 6/484* (2013.01); *G06T 5/002* (2013.01); *G06T 2207/10116* (2013.01)

(58) Field of Classification Search
CPC ....... A61B 6/5282; A61B 6/484; G06T 5/002; G06T 2207/10116
See application file for complete search history.

(56) References Cited

U.S. PATENT DOCUMENTS

| 2009/0060372 A1 | 3/2009 | Maton |
| 2009/0290779 A1 | 11/2009 | Knapp |

(Continued)

FOREIGN PATENT DOCUMENTS

| WO | WO2007148263 A1 | 12/2007 |
| WO | WO2014206841 A1 | 12/2014 |

(Continued)

OTHER PUBLICATIONS

PCT International Search Report, International application No. PCT/EP2018/070295, dated Sep. 19, 2018.

(Continued)

*Primary Examiner* — Edwin C Gunberg
(74) *Attorney, Agent, or Firm* — Larry Liberchuk

(57) ABSTRACT

An image processing system and related method. The system comprises an input interface (IN) for receiving dark-field image data obtained from imaging of an object (OB) with an X-ray imaging apparatus (XI). A corrector module (CM) of the system (IPS) is configured to perform a correction operation to correct said dark-field image data for Compton scatter to obtain Compton-Scatter corrected image data. The so Compton scatter corrected image data is output by an output interface (OUT) of the system.

7 Claims, 5 Drawing Sheets

(56) References Cited

U.S. PATENT DOCUMENTS

| | | |
|---|---|---|
| 2010/0091936 A1 | 4/2010 | David |
| 2010/0310037 A1* | 12/2010 | Wang ................. A61B 6/06 378/6 |
| 2011/0293064 A1 | 12/2011 | Huang |
| 2012/0257810 A1 | 10/2012 | Von Berg |
| 2014/0146935 A1 | 5/2014 | Goldammer |
| 2015/0243397 A1 | 8/2015 | Yun |
| 2016/0163072 A1 | 6/2016 | Koehler |
| 2016/0242726 A1 | 8/2016 | Koehler |

FOREIGN PATENT DOCUMENTS

| | | |
|---|---|---|
| WO | WO2016023782 A1 | 2/2016 |
| WO | WO2016177875 A1 | 11/2016 |

OTHER PUBLICATIONS

Yaroshenko A. et al, "Pulmonary Emphysema Diagnosis with a Preclinical Small-Animal Xray Dark-Field Scatter-Contrast Scanner", Radiology, vol. 269, No. 2, pp. 427-433, Nov. 2013.

Pfeiffer F. et al., "Hard X-Ray Dark-Field Imaging Using a Grating Interferometer", Nature Materials, vol. 7, pp. 134-137, Feb. 2008.

\* cited by examiner

SCATTER CORRECTION FOR DARK FIELD IMAGING

FIELD OF THE INVENTION

The invention relates to a system of image processing, a method of image processing, a computer readable medium and a computer program element.

BACKGROUND OF THE INVENTION

Dark-field imaging has attracted much interest especially in the medical field. Dark-field imaging is a type of X-ray imaging. Contrast in dark-field imaging relates to the amount of small angle scatter experienced by the X-radiation.

Experimental dark-field imaging with mice have been reported by A. Yaroshenko et al in "Pulmonary Emphysema Diagnosis with a Preclinical Small-Animal X-ray Dark-Field Scatter-Contrast Scanner", Radiology, vol. 269, No 2, November 2013.

SUMMARY OF THE INVENTION

There may be a need to improve dark-field imaging.

The object of the present invention is solved by the subject matter of the independent claims where further embodiments are incorporated in the dependent claims. It should be noted that the following described aspect of the invention equally applies to the image processing method, to the computer program element and to the computer readable medium.

According to a first aspect of the invention there is provided an image processing system, comprising:

an input interface for receiving dark-field image data obtained from imaging of an object with an X-ray imaging apparatus;

a corrector module configured to perform a correction operation to correct said dark-field image data for Compton scatter to obtain Compton-Scatter corrected image data, wherein the corrector module is configured to obtain the Compton scatter corrected image data by:

estimating a Compton scatter estimate data based on a transmission image data in relation to said object, and applying said Compton scatter estimate data to the dark-field image data or to underlying projection data from which the dark-field image data and transmission data have been reconstructed; and an output interface for outputting the Compton scatter corrected image data.

The correction operation performed by the corrector module is based on transmission data in relation to said object.

In other words, what is proposed herein is to improve quantitative evaluation in dark-field imagery by at least reducing or eliminating cross talk of Compton scatter into the dark-field signal as recorded during image acquisition. In other word, a residual Compton scatter contribution in the dark-field signal is computationally removed, or is at least reduced, by the proposed correction. This can be done in one embodiment by estimating the Compton scatter based on the associated transmission data, such as transmission data acquired of the same object. It is in particular this cross talk from Compton scatter signals into dark-field signals that is suspected to be responsible for image quality loss in relation to the dark-field signal, such as weak signal strength or weak signal distinctness. It has been observed that the dark-field signal distinctness decreases in the presence of Compton scatter, in particular the larger the path length through the object. The proposed image processing system helps increasing dark-field signal distinctness by reducing, or even removing, Compton scatter cross-talk in the dark-field signal to better quantify the underlying effect of small angle scattering. The corrected dark-field signal imagery allows also for better comparison with the transmission image, as the Compton scatter contribution, already present in the transmission image, has been removed or at least significantly reduced in the dark-field image. The corrected dark-field signal as proposed herein and the transmission image signal are hence complementary which allows for a better interpretation and quantitative evaluation of the two signals.

In one embodiment, the dark-field image data comprises image data reconstructed from projection image data acquired of said object.

In this embodiment, the corrector module is configured to obtain the Compton-Scatter corrected image data by:

estimating a Compton scatter estimate data based on the transmission data in relation to said object, and applying said Compton scatter estimate data to the dark-field image data.

In other words, the correction module operates in the image domain.

In an alternative embodiment, the correction includes processing the projection data. In other words, the dark-field image data comprises projection image data acquired of said object. In this embodiment, the correction operation by the corrector module includes:

estimating said Compton scatter based on the transmission image data reconstructable from said projection data or based on transmission data of the object otherwise obtained; and correcting said projection data based on the Compton scatter estimate.

The correction operation by the corrector module may further include:

reconstructing new dark-field image data from said corrected projection data.

In other words, a two-pass scheme may be envisaged in this embodiment.

In embodiments, the estimating of Compton scatter by the corrector module is adapted based on material or tissue type of the object.

According to a second aspect, there is provided an image processing method, comprising the steps of:

receiving dark-field image data obtained from imaging of an object with an X-ray imaging apparatus;

performing a correction operation to correct said dark-field image data for Compton scatter to obtain Compton-Scatter corrected image data; and outputting the Compton scatter corrected image data.

According to one embodiment, the correction operation is based on transmission data in relation to said object.

According to one embodiment, the dark-field image data comprises image data reconstructed from projection image data acquired of said object.

In this embodiment, the step of performing the correction includes:

estimating a scatter estimate, based on the transmission data in relation to said object, and applying said scatter estimate to the dark-field image data.

Alternatively, the dark-field image data comprises projection image data acquired of said object. If an interferometric imaging apparatus is used, the projection data is preferably acquired in a phase stepping operation, where a relative motion is induced between an interferometer and the object and/or X-ray beam. However, other, in particular non-interferometric, imaging systems, are also envisaged where no such phase stepping operation is required. For instance, in coded aperture imaging with aperture masks, no phase stepping is necessary (although this can still be done if desired) if aperture masks are suitably arranged spatially relative to the detector pixels.

In these embodiments, where the dark-field image data comprises projection image data, the step of performing the correction operation is partly performed in the projection domain and includes:

estimating a Compton scatter estimate based on the transmission image data reconstructable from said projection data or based on transmission data of the object otherwise obtained; and correcting said projection data based on the Compton scatter estimate.

In one embodiment, the performing of the correction operation further includes:

reconstructing new dark-field image data from said corrected projection data. In other words, in this embodiment, a two-pass scheme is used.

In embodiments, the estimating of Compton scatter is adapted based on material or tissue type of the object. Specifically, the Compton scatter estimate is differentiated according to tissue or material type to account for different Compton scatter characteristics. Specifically, a contribution to Compton scatter of a certain material/tissue of interest to the overall attenuation is determined and this is then used for the Compton scatter estimation. In embodiments, a correction value (eg, factor or offset-value) is estimated and this may be used to refine a first Compton scatter estimate. If this material-specific differential Compton scatter contribution is accounted for as proposed herein, an accuracy of the scatter estimate may be achieved. In particular, an improved dark-field signal may be obtained.

In the above embodiments, the associated transmission image/data is preferably likewise obtained together with the dark-field signal in the same reconstruction and/or from the same projection data. However, this is may not be so necessary in all embodiments, that is, the transmission data for the same object may be obtained differently from the dark-field signal, e.g., in a different reconstruction and/or from different data and/or by using different imaging equipment, etc.

In all of the above, the Compton Scatter estimate (data) may be in supplied in the form or scatter fractions, but other formats are not excluded herein. The "applying" of the Compton Scatter estimate to the dark-field image data to effect the correction may include any suitable arithmetical operation (subtraction, division, etc).

The wherein an imaging apparatus for performing the imaging includes, but is not limited to: i) a full-field-of-view X-ray imaging apparatus or ii) a slot-scanning X-ray imaging apparatus.

In a third aspect there is provided an imaging arrangement, comprising an image processing system as per any one of above mentioned embodiments and an X-ray imaging apparatus.

According to a fourth aspect there is provided a computer program element which, when being executed by a processing unit, is adapted to perform the method steps.

According to a fifth aspect there is provided a computer readable medium having stored thereon the program element.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
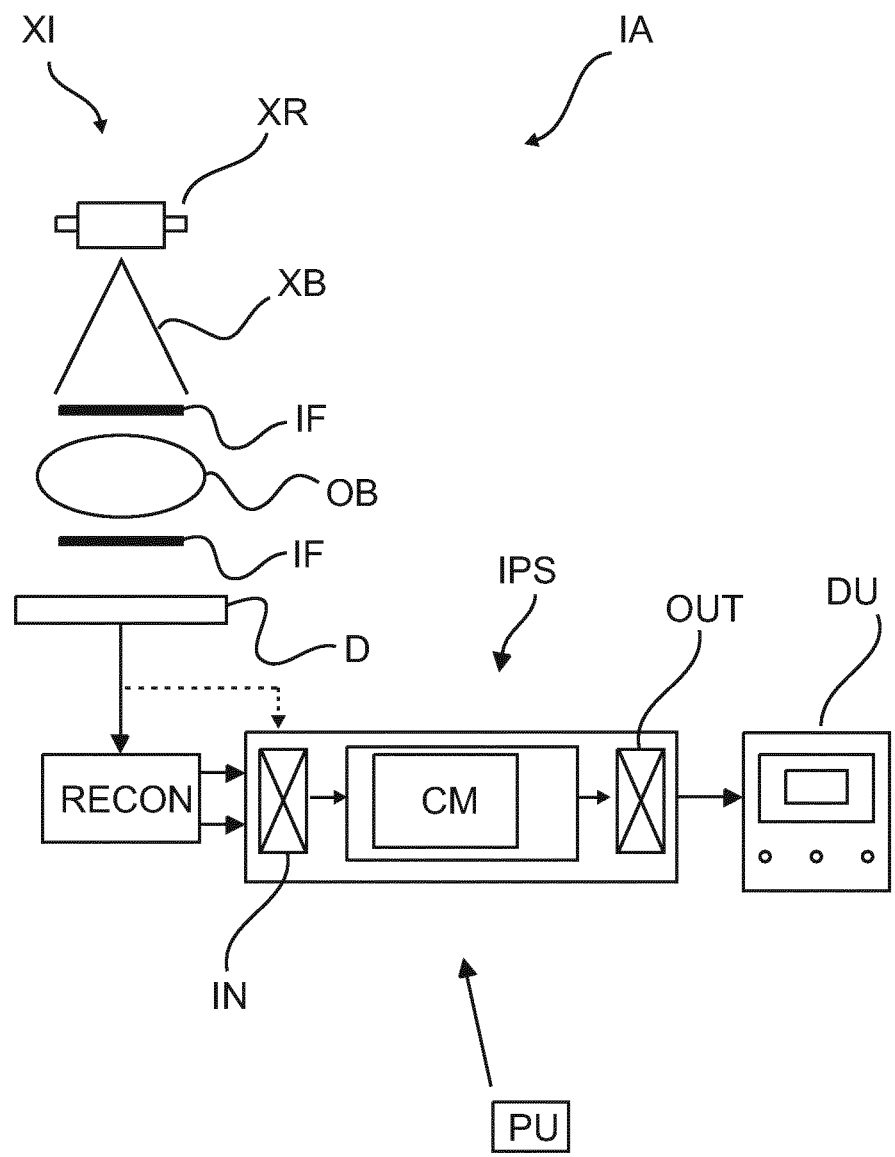
FIG. 1 shows a schematic block diagram of an imaging arrangement for dark-field imaging.

With reference to FIG. 1, there is shown a schematic block diagram of an image processing arrangement IA that includes a computerized image processing system IPS and an X-ray imaging apparatus IA. The X-ray imaging apparatus is configured for dark-field imaging.

The image processing system IPS may be runs as one or more software modules or routines on one or more processing units PU such as one or more computers, servers, etc. The IPS may be arranged externally and remote of the imager XI or the IPS is integrated into the imager XI, for instance into a computing unit PU of the imager XI, such a work station. The image processing system IPS may be implemented in a distributed architecture to serve a group of imagers suitably communication network. Alternatively, some or all components of the IPS may be arranged in hardware such as a suitably programmed FPGA (field-programmable-gate-array) or as hardwired IC chip.

Broadly, the imaging processing system IPS processes in particular dark-field imagery produced by the imaging apparatus IA to produce Compton scatter corrected dark-field imagery. The corrected image can then be displayed on a display unit DU or can be stored in a memory for later review, or can be otherwise further processed.

Although in FIG. 1 it is envisaged that the imaging apparatus IA supplies direct via wireless or a wired connection the imagery to the image processing system IPS, this may not be so in all embodiments. For instance, the imagery may be first stored in a memory such as a PACS of a HIS or otherwise and the imagery to be processed is retrieved at a later stage (e.g. upon user request) by the IPS and is then processed.

The imagery obtainable by the image processing system IPS has the benefit that cross talk (in the sense of residual signal contributions) from the Compton scatter contribution into the dark-field signal can be reduced. In other words, in the processed image as supplied by the proposed IPS, a better separation between Compton scatter and Raleigh scatter can be achieved. The input imagery (the dark-field image and the attenuation image) is supplied preferably by an interferometric imaging apparatus AI. However, other, non-interferometric imaging systems, such as coded aperture systems, may also be used instead that are also capable of producing at least the dark-field signal, and preferably, in addition thereto, the transmission image signal. The dark-field signal is either produced by the imaging system direct or is at least reconstructable from suitable projection or other data acquired by the imaging system.

In a preferred embodiment the interferometric imaging apparatus AI includes an X-ray source XR and an X-radiation sensitive detector D. The imager IA can be 2D or 3D (such as a CT scanner). Between the X-ray source XR and the detector D there is defined an imaging region where the object OB (e.g., the chest of the subject) to be imaged resides during imaging. In the imaging region there is also arranged an interferometer IF that includes a single, two or more grating structures. Periodicity, aspect ratio, etc. of the gratings are such that they cause diffraction of the X-ray beam and/or just enough coherence is achieved so that the small-angle scattering can be detected or derived. Absorption and phase gratings may be used. In one embodiment the gratings are formed by photolithography or cutting in silicon wafers to define a periodic pattern of trenches. Interspaces between the trenches may be filled with lead or gold for the absorption gratings. Instead of such gratings, crystal structures may be used.

In one embodiment, an additional grating structure is arranged between the detector D and the object OB whilst the other grating is arranged between the object OB and the X-ray source XR. In some embodiments there is also an additional grating arranged at the X-ray source, in case the X-ray source is incapable of generating natively coherent radiation. If the X-ray source produces incoherent radiation (which is usually the case), the (absorption) grating at the X-ray source (also referred to as the source grating) transforms the X-radiation coming out of the X-ray source into an, at least partly coherent, radiation beam XB.

The at least partly coherent radiation beam XB propagates through the imaging region and interacts with the interferometer and the object OB. After said interaction, the radiation is then detected in form of electrical signals at radiation sensitive pixel elements of the detector D. Data acquisition circuitry digitalizes the electrical signals into projection (raw) image data which is then processed by the IPS in a manner explained in more detail below. The imaging apparatus XI may be of the full field-of-view (FoV) type as shown in FIG. 1 where the detector is of the flat panel type. In full FoV imaging system, the size of the detector D corresponds to the desired FoV. Alternatively, the detector may be smaller than the intended FoV such as in slot-scanning systems. In some these system, the detector comprises a discreet series of detector lines. The detector lines are mounted on a scan arm to be scanned across the intended FoV in different slot-positions. Slot-scanning systems are more cost effective than full FoV system because they require smaller detectors and smaller gratings IF. The gratings are mounted on the scan arm above the detector and are equally scanned across the FoV. In alternative slot-scanning systems, although the detector D has the same size as the desired FoV, the gratings are smaller and a collimation is used to scan only parts of the FoV (in "slots") at any one time as per the collimation. In a full FoV system, there is a simple one-to-one relationship between pixel position and imaginary geometrical rays that pass through the imaging region to define the imaging geometry. The rays extend from a focal spot of the X-ray source XR and intersect the detector plane at the respective pixel positions. Each one of the geometrical rays corresponds to a respective, different, single one of the pixels. No such simple relationship exists in slot-scanning system, where each geometrical ray is seen by many different pixels in different "slots" during the scanning. Signals from different pixels are then processed together by a suitable logic for any single geometrical ray.

Generally, when X-radiation interacts with material, it experiences both attenuation and refraction. The attenuation on the other hand can be broken down into attenuation that stems from photo-electric absorption and attenuation that comes from scatter. The scatter contribution in turn can be decomposed into Compton scattering and Raleigh scattering. For present purposes it is the Raleigh scattering (or sometimes called small angle scattering) that is of interest. It is the amount of Raleigh scattering that is modulated in the dark-field signal.

The attenuation can be understood as $=I_0 * e^{-\mu_L * h}$, with $\mu_L$ the absorption constant of lung tissue, and with h being the in-tissue path length through the object. The attenuation signal as recorded in the attenuation image is then $T=I/I_0$, with $I_0$ being the initial reference intensity before entering the lung tissue and I the intensity actually recorded at detector D.

The dark-field contribution can be modelled as visibility $V=V_0 * e^{-\varepsilon_L * z}$, with $\varepsilon_L$ a diffusion constant for lung tissue, z=the in-tissue path length as above, and $V_0$ being the reference visibility without object interaction (recorded in a calibration measurement). The dark-field signal as recorded in the dark-field image is then $D=V/V_0$.

Traditional radiography systems are usually incapable of resolving the detected signal into dark-field contribution. But by using the interferometer as shown in FIG. 1 it is possible to translate these contributions into an intensity pattern of fringes which can be analyzed by a reconstructor RECON. Reconstructor RECON computationally splits up the detected fringe pattern in the projection data into three contributions or signals, namely the refraction contribution (also referred to as the phase contrast signal), the dark-field signal component and a remaining attenuation component. Ideally, there should be a clear separation of the Raleigh scatter in the dark-field signal from Compton scattering and absorption as captured in the attenuation channel.

Figure 2:
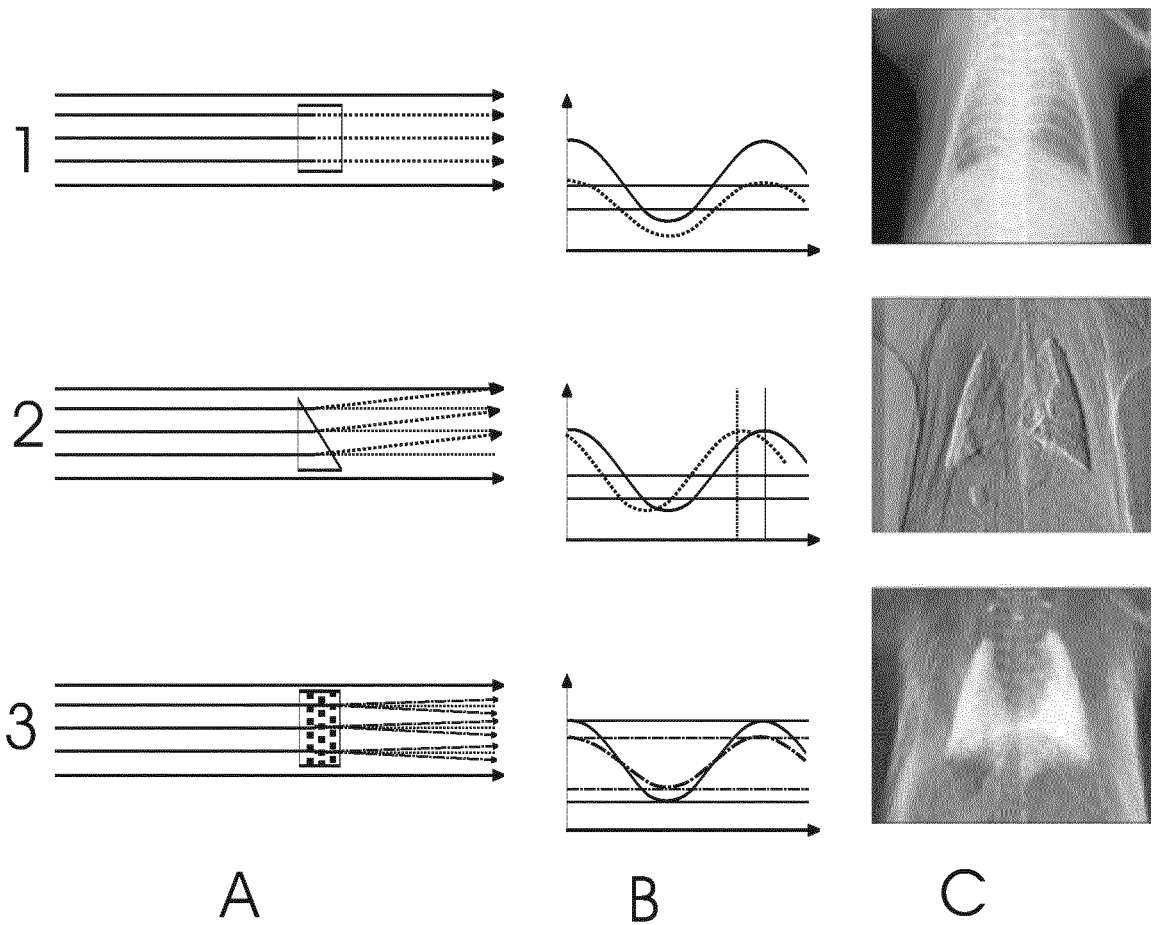
FIG. 2 is an overview of various manners of interaction of X-ray radiation with a matter.

The signal processing by the reconstructor RECON of the detected intensities at the detector into the three signal channels (phase contrast, dark-field and attenuation) has been covered elsewhere such as by F Pfeiffer et al in "Hard-X-ray dark-field imaging using a grating interferometer", *Nature Materials* 7, pp 134-137 (2008). In Pfeiffer et al and other similar techniques as envisaged herein in some embodiments, a Fourier technique is used to analyze the fringe pattern in the projection data as detected at the detector D. In these types of imaging system, the capability for dark-field imaging is achieved as follows: the projection data is acquired at the detector D during a phase stepping operation. The phase stepping operation induces a motion between X-ray beam and interferometer and/or the object OB. For instance, in one embodiment the analyzer grating (that is, the grating arranged between object and detector) is moved ("scanned") laterally relative to an optical axis of the X-ray beam. Alternatively, phase stepping can also be achieved by moving the object OB, or by moving the X-ray source, etc. This motion causes a change of the fringe pattern which in turn can be recorded in a corresponding series for each step of the motion ("phase stepping"). This series of measurements form, for each geometrical ray, an associated phase curve. The phase curves are in general of sinusoidal shape and it has been found that each encodes the quantities of interest, in particular the dark-field signal, along with attenuation and phase change. FIG. 2 illustrates this: Specifically, FIG. 2 is a schematic illustration of the various manners of interaction of X-radiation with matter. FIG. 2 includes nine panes arranged in a matrix, with three rows labeled "1", "2", "3" and columns labeled "A", "B", "C".

Pane 1A (in the top, leftmost position) illustrates the effect of attenuation represented by linear attenuation coefficient. This quantity relates to density and effective atomic number in the matter.

Pane 1B shows the effect of attenuation on the phase curve and how a change in attenuation influences the phase stepping curve. As the phase stepping curve graphs intensity in vertical direction versus grating position in a horizontal direction. As can be seen, a change in attenuation results in a horizontal shift of the curve that is decreased attenuation throughout.

Pane 1C shows exemplary attenuation imagery, in this case an image taken of a mouse thorax.

Referring now to the second row, pane 2A in particular, this illustrates the physical effect of refraction in pane 2B and its effect on the phase curve. A change in refraction (phase gradient) results in the phase curve being shifted horizontally. The refraction experienced by the X-radiation may be represented by the refractive index decrement $\delta$ which relates to the electron density $\rho_e$.

Pane 2C shows an exemplary phase contrast image of the mouse thorax.

In the last row (row 3), pane 3A illustrates small angle scattering which is the effect that confers contrast in dark-field imaging. Small angle scattering is among other effects assumed to be caused by small micro-structures that are usually below the resolution limit. Such microstructures can be found for instance in spongy or porous tissues such as in lung tissue. As can be seen, the influence on the phase curve is such that it increases amplitudes as represented in pane 3B. Pane 3C finally shows an exemplary dark-field image of the mouse thorax.

The phase curves can be respectively analyzed, for instance by fitting to a sinusoidal model as described in Pfeiffer et al to effect the reconstruction. Preferably, there are at least three fitting parameters included in the sinusoidal model. The three fitting parameters represent, respectively, the three contributions phase contrast, dark-field signal and transmission. The sinusoidal model is fitted by reconstructor RECON to the phase curves to so compute in particular the dark-field image and the transmission (also called "attenuation") image. Specifically, during reconstruction in a full FoV system, the phase curve for each pixel/geometrical ray is preferably directly used to obtain the transmission and dark-field information for each pixel. Any curve fitting numeral technique such as least squares, gradient descent, maximum likelihood, etc. can be used for this. The phase contrast signal, although sometimes of interest in its own right, will be disregarded herein. This type of reconstruction algorithm is sometimes referred to as "phase retrieval" but this is for present purposes a misnomer as it is also the transmission image and the dark-field image that are also reconstructed in phase retrieval and it is the dark-field imagery that is of primary interest herein. Although grating based X-ray imaging is preferred herein, other, in particular non-interferometric techniques capable of providing a dark-field signal and, preferably, the associated transmission image signal, are also envisaged herein, such as coded aperture systems. In general, in grating/mask based imaging techniques, the dark-field imaging is obtained through imparting a periodic wave-front modulation on the incoming imaging X-ray beam and a measurement, by the X-ray detector D, of a variation of the resulting wave-front caused be the object to be imaged. In addition, non-grating imaging techniques are also envisaged herein.

The reconstructor RECON outputs the dark-field signals and the attenuation signals as respective arrays of image values which form the dark-field image and the transmission image, respectively. These image values or pixel values represent respectively the contrast for the dark-field signal and the attenuation experienced by the X-radiation, for the respective geometrical ray. More particularly, and for the full FoV system, at a certain pixel position (x,y) there is associated a certain value in the dark-field image and that value should ideally represent the amount of small angle scattering observed at the respective position x,y of the detector plane. The same pixel position x,y in the transmission image on the other hand is expected to represent the amount of attenuation experienced due to Compton scatter and photo-electric absorption.

However, it has been observed that the separation between the Compton scatter signal and the dark-field signal is not as clear cut as one may wish for. In particular, it has been found that the signal of Compton scattered photons will create an additional, spurious dark-field signal because Compton scattering is incoherent and much of the accuracy of the interferometric set-up rests precisely on the assumption of coherent radiation. This spurious dark-field signal is caused by a cross-talk contribution from the Compton scattering. The undesired Compton cross talk into the dark-field signal creates a superimposed fringe pattern. This cross-talk impedes quantitative assessment of the small angle properties of lung tissue, which is important for instance in image based diagnostic examination of lung diseases such as Chronic Obstructive Pulmonary Disease (COPD) and fibrosis and others.

The proposed image processing system IPS is configured to combat these issues and to create a dark-field image which is corrected for the Compton scatter influence. In other words, the Compton scatter corrected dark-field image produced by the proposed imaging system has a better signal distinctness as the disturbing cross-talk of the Compton scatter has been reduced or even removed.

Turning now in more detail to the proposed image processing IPS and with continued reference to FIG. 1, this includes a correction module CM to reduce or ideally remove from the dark-field signal (DAX) cross talk from the Compton signal. Broadly, input imagery is received at an input interface IN of the signal processing system IPS. The input imagery comprises the dark-field image and the transmission image, preferably both as reconstructed by the re-constructor RECON.

The correction model CM then performs a correction operation on the received dark-field image to produce corrected dark-field image. The corrected dark-field image is then output at output port OUT.

At least two different embodiments are envisaged for the correction module CM. In one embodiment the correction module estimates the amount of Compton scatter from the transmission image. This can be done by establishing the scatter fraction pixel-wise. The scatter fraction is then arithmetically applied to the as yet Compton scatter corrupted dark-field image as received at the input IN. More particularly, in one embodiment the respective scatter fractions are estimated from different pixel locations in the transmission image and are then pixel-wise applied at the corresponding pixels to the dark-field image by subtraction. In other words, a scatter fraction map obtained from the transmission image is subtracted from the dark-field image to produce the corrected dark-field image. Other arithmetical operations such as division, multiplication are also envisaged.

An alternative embodiment for the correction module CM is also envisaged and this is shown in dashed lines in FIG. 1. In this embodiment the correction module CM acts on the projection image data. More particularly, the correction module CM in this embodiment operates in concert with the re-constructor RECON to implement a two-pass reconstruction to effect the Compton scatter correction. More particularly, the scatter contribution is again estimated as described previously in the first embodiment. However, the scatter information (e.g., scatter fraction) is now not applied to the reconstructed dark-field image, but is applied instead to the underlying projection data from which the two images received at the input port IN have been reconstructed. The so corrected projection data is then forwarded to the re-constructor RECON again and is there reconstructed once again in the second pass to obtain the corrected dark-field image, alongside the imagery for the other channels, transmission and phase contrast, the latter two being of lesser relevance herein.

Figure 3:
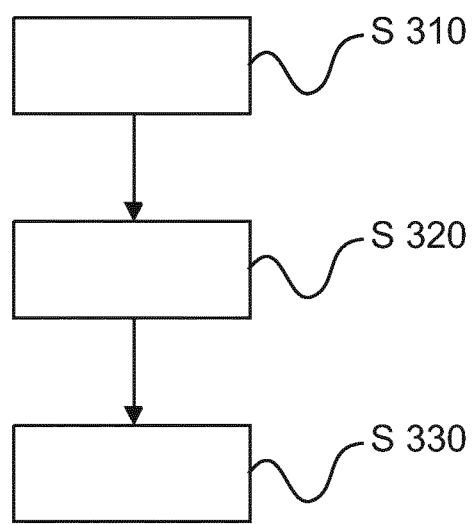
FIG. 3 is a flow chart of a method of image processing.

Referring now to FIG. 3, this shows a flow chart of a proposed image processing method that underlies operation of the image processing system IPS of FIG. 1 and provides further details of said operation. It will be understood however, that the method steps described in the following constitute a teaching in their own right and are not necessarily tied to the specific architecture shown in FIG. 1.

Broadly the proposed new image processing method for the correction, that is the reduction removal of Compton scatter influence in dark-field imagery includes step S310 where the input dark-field image data is received. The input DAX imagery is presumably Compton Scatter corrupted.

The dark-field image data have been obtained, by operation of an X-ray imaging apparatus, of an object of interest OB, such as a lung of a human or animal patient or other.

At step S320 the correction operation is performed on the dark-field image data to obtain Compton scatter corrected dark-field image data. In this Compton scatter correction dark-field image data, spurious signals stemming from Compton scatter image has been removed, or at least reduced.

At step S330 the so Compton scatter corrected dark-field image data is then output and can be further processed, such stored or viewed etc.

Two basic embodiments are distinguished herein. The received dark-field image data is either reconstructed from previously acquired projection data or the dark-field image data is included in the projection data. In both embodiments, an associated transmission image is used to obtain the information on the amount Compton scatter. Preferably this transmission image is associated with the dark-field image data as is the case for instance in the previously mentioned phase retrieval algorithm which will be described in more detail below at eqs (7)-(12). However, in other embodiments the transmission image is still obtained of the same object as the dark-field image data but otherwise bears no relation with said dark-field image data. The transmission image could have been obtained previously by a completely different method and/or imaging apparatus but, preferably still of the same object in preferably the same imaging geometry as for the dark-field image data.

Figure 4:
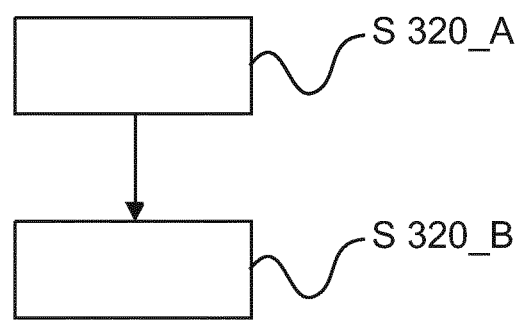
FIG. 4 is a flow chart of a correction operation according to a first embodiment as used in the method of FIG. 3.

In the first embodiment where the correction step is performed on reconstructed dark-field image data, the correction step S320 comprises the following sub-steps as per the flow chart of FIG. 4.

At step S320A a scatter fraction or other quantity related to the Compton scatter is estimated based on the transmission image for the same object.

At step S320B, the scatter estimate, eg scatter fraction, is then applied to the dark-field image data to so effect the correction. Application of the scatter fraction information includes pixel-wise subtraction or other suitable arithmetical operations. For instance, if the image data is in the logarithmic domain as preferably the case, a subtraction of the scatter fraction from the measured dark-field image data is performed. Otherwise, if no logarithm is used, the received dark-field image data is divided pixel-wise by the respective scatter fraction amount for the respective pixel.

As observed earlier, Compton scatter is in general involved in DAX imaging even when using an anti-scatter-grid. Compton Scatter leads to contrast loss in the transmission image as usual but it has been found that it is also the Visibility V and the dark-field signal D that are reduced by the same factor. One may therefore correct both data channels as follows:

$$I_{ScatterCorrected} = I_{measured} - S \quad (1)$$

$$(I_{ScatterCorrected} = P; \text{ i.e. } I_{ScatterCorrected} = \text{measured} * (1-SF)) \quad (2)$$

and $$T_{ScatterCorrected} = I_{ScatterCorrected}/I_0 \quad (3)$$

or $$\log(T_{ScatterCorrected}) = \log(T_{measure}) + \log(1-SF) \\ (T_{ScatterCorrected} < T_{measured}) \quad (4)$$

$$D_{ScatterCorrected} = D_{measured}/SF \\ (D_{ScatterCorrected} > D_{measured}) \quad (5)$$

or $$\log(D_{ScatterCorrected}) = \log(D_{measured}) - \log(SF) \quad (6)$$

In other words, when not in the log-domain, the scatter fraction is pixel-wise divided or multiplied with the pixel values of the dark-field image D to effect the correction (eq (5)). If in the log-domain (eq (6)), the scatter fraction contribution is subtracted pixel-wise. In the above correction algorithms, the (additional) correction of the transmission image at eq (1)-(4) is optional herein. Any algebraically equivalent reformulations of the above correction algorithms (1).(6) are equally envisaged herein.

The scatter fraction SF itself can be estimated from the transmission image by known scatter estimation techniques. For instance, in one embodiment the scatter fraction SF is estimated from a physical model of the radiation, the measured transmission and local gradients in the measured intensities I. In general, the Compton scatter correction is done such that $\log(P)=\log(I)+\log(1-SF)$ so as to compensate for the contrast loss due to Compton Scatter. See also the explanations/definitions of term in the appendix. Further details on scatter fraction estimation can be found in WO 2007/148263 where scatter is estimated based on water ball phantoms. Other materials than water may be used instead. In addition, scatter correction schemes are than phantom-based are also envisaged. In these or similar types or scatter estimation techniques, scatter kernels are pre-computed and held in a database. The scatter kernels represent scatter in relation to different phantom bodies of different sizes and/or orientation (such as the mentioned water balls). A transmission characteristic of the phantom body may be matched (locally or globally) to the transmission image to find the best match. The kernel associated with the matching phantom body is then used as the (Compton) scatter estimate. This type of phantom-based scatter estimation may also be used in the following embodiments.

Figure 5:
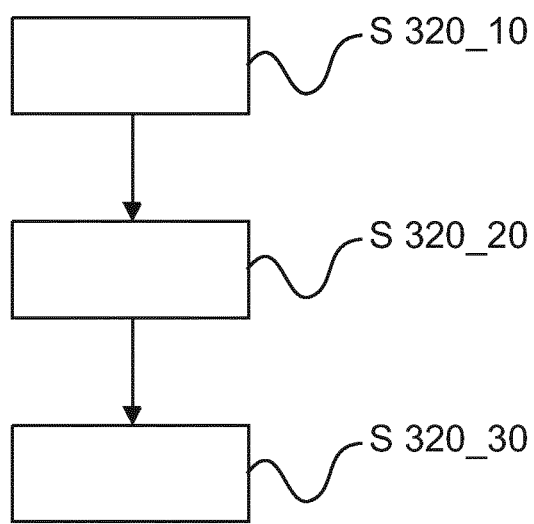
FIG. 5 is a flow chart for a correction operation according to a second embodiment as used in the method of FIG. 3.

Turning now to the second embodiment where the correction in step S320 operates at least partly on the projection data. As mentioned above, the correction step in this embodiment is a "two-pass/step" algorithm. More specifically, in a first pass, a conventional, intermediary, transmission image, presumably suffering from Compton scattering, is generated by reconstruction from projection data. This first pass image is then used to estimate by means of known Compton scatter correction techniques (such as the ones mentioned above), the Compton scatter signal in the intermediate image. It has been found, that in very good approximation, the Compton scatter signal does not depend on the relative grating position. Therefore, this estimate can be used to correct the projection data and a subsequent reconstruction can be used to obtain an improved DAX signal. In an interferometric setting, the projection data to be corrected is formed from the obtained phase curve in the phase stepping scan, and the reconstruction corresponds to the mentioned phase retrieval algorithm. The flow chart in FIG. 5 summarizes the sub-steps involved in the this 2-pass correction step.

Initially, X-ray projection data is acquired of the object of interest by exposure to X-ray and detection at X-ray detector D.

At step S320_10 the Compton scatter is first estimated on transmission data reconstructed from the projection data.

At step S320_20 the correction is then performed on the projection data based on Compton scatter information as estimated in step S320_10.

In step S320_30 then another reconstruction is performed and, based on the so corrected projection data, the corrected dark-field image is obtained.

As mentioned above the reconstruction can be done using the fitting operation as explained above. Alternatively, any other reconstruction method capable of computing dark-field imagery can be used instead. If phase stepping operation is involved as in the interferometric setup, as explained above in relation to FIG. 1, the projection data include the phase curves.

Also, it should be clear from all of the above embodiments, that it is not necessary herein for projection data acquisition to occur directly before the above described steps are carried out, although this can still be done in a real-time or online setting. Alternatively, the projection data had been acquired well before (minutes, hours or days) the above described steps were carried out, with the projection data then retrieved form storage as required.

With particular reference to a full field of view system, the correction steps as per flow chart FIG. 5 can be understood in more detail as follows. In the full FoV case, the signals D and T are derived in the first pass from the raw data R, by fitting the following model to them on a per-pixel basis ("i" being a phase stepping index):

$$R_i = TI_0(1 + DV_0 \cos(\alpha_0 + i\Delta\alpha)) \quad (7)$$

A standard sinusoidal model comprises three dedicated fitting variables for the three contributions of: transmission (T), dark-field (D) and phase change ($\alpha$). As mentioned above, the modelling ansatz (7) is incomplete as there is an additional Compton scatter background signal S, which is independent of the grating position. This contribution may hence be included as an additive term to yield a new model:

$$R_i = TI_0(1 + DV_0 \cos(\alpha_0 + i\Delta\alpha)) + S, \text{ with } T^*I_0 = P \quad (8)$$

The new model with Compton scatter contribution as per expression (8) can be reformulated into:

$$R_i = (TI_0 + S)\left(1 + \frac{I_0 T}{I_0 T + S} DV_0 \cos(\alpha_0 + i\Delta\alpha)\right) \quad (9)$$

It is convenient to consider not the absolute amount of scatter, but the so-called scatter fraction, which is defined as $$SF = \frac{S}{S + P}$$

Using this definition, the factor in front of $DV_0$ in Eq. (9) can be written as $$\frac{I_0 T}{I_0 T + S} = 1 - SF \quad (10)$$

Therefore, the first estimated value for D as per the first pass reconstruction by fitting to (8) is wrong by a factor 1−SF. We propose then that correction can be simply applied using the result of the scatter correction on the mean signal ($TI_0 + S$): In other words, $R_i$ is corrected for each i as per $$R_{i_{scatterCorrected}} = R_i - S \quad (11)$$

or the scatter information S is otherwise suitably arithmetically combined pixel-wise with the original projection data $R_i$.

The corrected projection data $R_{i_{scatterCorrected}}$ as per Eq. (11) is then fitted in the second pass correction to a new sinusoidal model as per:

$$R_{i_{scatterCorrected}} = TI_0(1 + DV_0 \cos(\alpha_0 + i\Delta\alpha)) \quad (12)$$

In the above formulae, there is in general a dependency of the reference data ($I_0$, $V_0$ and $\alpha_0$) on pixel position "i", but the index has been dropped in the above for the sake simpler notation.

The above formalism can also be applied to a slot-scanning system where processing is not per pixel position i, but per geometrical ray which includes consolidating all the projection data as sensed by different pixels but associated with the same given geometrical ray. Notably, in this embodiment, the scatter estimation is performed on the reconstructed transmission image for each slot position separately, but not for the entire FoV. The same scatter estimation techniques can be used as mentioned above. The obtained scatter as estimated for the various slot positions are then subtracted from, or otherwise arithmetically combined with, the projection raw data for the respective slot position to obtain the corrected projection data. The second pass reconstruction is then performed with the so corrected projection data and the model given in Eq. 8. It should be understood form the above that the dark-field, the transmission and the phase image are produced by the same algorithm (phase retrieval) but this may not be necessarily so in all embodiments. Other embodiments are also envisaged, where the associate transmission image is produced by a different algorithm and/or by a different imager, etc. It should be ensured however that the dark-field image and the transmission image are acquired of the same object, preferably at the same time and in the same imaging geometry. However, transmission image and the to be corrected dark-field image may well be acquired or produced at different times, with the transmission image being retrieved form an image memory, database (of a PACS (picture archiving and communication system) of a hospital information system (HIS) or other) when the instant dark-field image is to be Compton scatter corrected.

Although in the above the term "reconstruction" was used mainly as a reference to the phase retrieval algorithm with curve fitting to phase stepping data, other reconstruction algorithms capable to yielding a dark-field signal are also envisaged herein. These other reconstruction algorithms may, or may not yield also the associated transmission image, they may or may not involve phase stepping and/or they may or may not involve gratings structures such an interferometer, etc. The associated transmission data may be obtained through other reconstruction algorithms and or other imaging equipment.

In one embodiment the scatter corrected dark-field imagery as obtained from the above can be used in addition together with a beam hardening correction algorithm and/or an additional algorithm that accounts for the "biasing effect". The biasing effect relates to the fact where that at low X-ray dose with high relative impact of quantum noise, the Visibility measurement leads to too high values for V and as such for D. In other words, the proposed correction system IPS and method can be used in combination with the mentioned other two correction algorithms to even further improve dark-field signal distinctness to account for the three known effects that unfavorably weaken dark-field signal distinctness: Compton scatter (as proposed herein), beam hardening and biasing.

The Compton scatter estimating in any one of the above mentioned embodiments in FIGS. 1-5 may be refined by tissue type differentiation. More specifically, the Compton scatter estimate takes into account specific tissue types at a given image location. Yet more specifically, and in embodiments, an amount of bone is measured to establish a bone fraction and the Compton scatter estimate is then adapted per image location based on the (local) bone fraction measurement. The bone fraction (a number) may be estimated using extant bone identification techniques such as described in Applicant's US 2012/0257810.

Compton scatter estimation based on bone fraction adaptation allows achieving yet more accurate dark-field imaging results. This is because different tissue types/material cause different amounts of Compton scatter. In particular, soft tissue and bone cause markedly different amounts of Compton scatter. Yet more specifically, the photo-electric effect contributes more to the attenuation for bones than for water, for instance. In other words, a water object creates more Compton scattering than a bone object with the same total attenuation. This effect is even more prominent for low energies where the photo-electric effect contributes significantly to the total attenuation. This type of low energy setting is applicable in particular for dark-field imaging, where the imaging apparatus IA is typically operated at tube voltages around and below 70 keV. In other words, in phantom based scatter estimation techniques (such as the water ball method mentioned above), there is a tendency to systematically wrongly estimate (in particular overestimate) Compton scatter.

It is proposed herein in one embodiment to identify by image processing location(s) of bones as per the radiographic images in order to identify image areas with contribution of bones to the total attenuation. This step may be implemented by using virtual (that is, image based) ribcage removal techniques such as Applicant's US 2012/0257810 or other image processing techniques such as described in US 2009/0060372 or US 2009/0290779. Applicant's bone removal algorithm as per US 2012/0257810 is configured to remove ribs only. Preferably, but optionally, other bone portions such as the vertebra are not detected and removed from the image. Such is also envisaged herein, so that certain materials or tissue types (such as bone or others) are virtual removed in the image processing, only in a predefined region or interest (such as the chest).

Whatever the bone removal algorithm used, it is envisaged herein that these algorithms allow estimating a respective contribution of soft tissue and bone to the total attenuation. With this knowledge, Compton scatter can be now estimated and corrected independently for soft tissue and bone. This result will yield better quantitative values that can be used for disease severity estimation. In more detail, the Compton scatter estimation as performed by the correction module CM or in step S320A, S320_10 above may include in embodiments the following sub-steps:

a) identifying areas in the transmission image (in image or projection domain) that represent bone;
b) estimating an amount (eg in percentage) to which bone contributes to the total transmission as measured in the transmission image to arrive at a bone fraction value, either for the whole image or per image location (voxel or pixel);
c) replacing a respective through-bone-path-length by a Compton-scatter equivalent path-length through water used for the water-phantom based scatter correction/estimation. In this sub-step one may use the known differential photoelectric attenuation of bone vs. water for determining a correction factor for the measured intensity (i.e. scatter-less attenuation of the beam);
d) choosing a precomputed scatter kernel, preferably from a pre-defined data base, that best matches the (at step c)) determined water-thickness equivalent.

These steps make the Compton scatter correction more accurate when large and thick bones are involved. Specifically, since bone consists of a mix of water-like tissue and bone mineral (such as Hydroxylapatite $Ca_5(PO_4)_3OH$), the components Calcium (Ca) and Phosphorus (P) cause a higher contribution of photoelectric absorption to the total attenuation. It is thus expected that the adapted scatter correction will result in a lower (but more accurate) Compton scatter estimation.

Sub-steps c), d) are optional and applicable in particular for phantom-body based scatter estimation techniques such as the water ball based method. Step a) is also optional if the contribution of bone (or other material/tissue type of interest) to the overall transmission can be estimated otherwise without localization.

The correction factor in step c) may be computed in proportion to the amount of bone found.

In an alternative embodiment, we propose to harness the observation that scatter from soft tissue and bone are additive in good approximation. Using this observation, the scatter contribution can be estimated from a soft-tissue image and a bone image independently using different scatter kernels (for soft-tissue and bone, respectively) and the two contributions are then added. The soft tissue image and the bone image may be obtained by any of the above referenced bone identification algorithms. Once the bone image is gotten, this is subtracted from the overall input transmission image to so derive the soft-tissue image.

It will be understood that in the above main reference has been made to bone fraction versus soft-tissue in relation to Compton scatter estimation as this is of particular relevance for lung imaging. However, in other imaging contexts, the above described differentiation and refinement of Compton scatter estimation may be readily applied to materials/tissue other than bone/soft-tissue and such embodiments are also envisaged herein. Equally, although the above has been described with particular reference to phantom-based scatter estimation techniques, other scatter estimation approaches are also envisaged herein.

One or more features or components of the IPS as disclosed herein may be configured or implemented as/with circuitry encoded within a computer-readable medium, and/ or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system PU.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit PU can be adapted to operate automatically and/or to execute the orders of a user. A computer program may be loaded into a working memory of a data processor. The data processor may thus be equipped to carry out the method of the invention. This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

| Appendix: Definition of terms | |
|---|---|
| I | Intensity of X-ray on the detector behind the object |
| $I_0$ | Intensity of X-ray on the detector with no object |
| $T = I/I_0$ | Transmission of the object; |
| V | Visibility = contrast of the fringe behind the object |
| $V_0$ | Visibility = contrast of the fringe with no object in blank scan |
| $D = V/V_0$ | Dark-field Signal. D is equivalent to a Contrast. For instance, in a suitable mapping, D = 1 means "no scattering material in the beam" |
| $DAX = -\log(D)$ | This DAX-signal is proportional to the amount of scattering material in the beam. DAX = 0 means no such object. |
| P | Primary signal, the fraction attenuated of X-ray intensity that "makes the true signal" |
| S | Compton scatter radiation. This is the amount of X-ray behind an object that stems from Compton-scattered radiation and lowers the contrast of the image |
| $I = P + S$ | |
| $SF = S/(S + P)$ | Scatter fraction. It is the percentage of scatter in the total signal. SF can be up to 95% for a heavy object without an anti-scatter-grid. In DAX images it can still be of the order of 10%. |
| $\log(SF) = \log(S) - \log(I)$ | |
| $C_{ScatterCorrected} = 0.5 * (P_{object} - P_{background})/(P_{object} + P_{background})$ | Contrast of an object due to Primary radiation alone |
| $C_{measured} = 0.5 * (I_{object} - I_{background})/(I_{object} + I_{background})$ | Contrast of an object in the measured Intensity. |
| $C_{ScatterCorrected} = C_{measured} * (1 - SF)$ | (1 − SF) is the Contrast-loss-factor. |
| $P = I - S$ $P = I * (1 - SF)$ | Basic scatter correction formula in the linear domain. Alternatively, only a fraction of S is subtracted as this has been shown to yield good results. |
| $\log(P) = \log(I) + \log(1 - SF)$ | Scatter Correction in the log-domain. |

The invention claimed is:

1. An image processing system, comprising:
an X-ray imaging apparatus configured to image an object;
an input interface for receiving dark-field image data obtained from the imaged object;
at least one processor configured to perform a correction operation to correct said dark-field image data for Compton scatter to obtain Compton-Scatter corrected image data by:
estimating a Compton scatter estimate data based on a transmission image data in relation to said object, and applying said Compton scatter estimate data to the dark-field image data or to underlying projection data from which the dark-field image data and/or transmission data have been reconstructed; and an output interface for outputting the Compton scatter corrected image data.

2. The image processing system of claim 1, wherein the at least one processor is further configured to reconstruct Compton-Scatter corrected image data from said corrected projection data.

3. The image processing system of claim 1, wherein the Compton scatter estimate data is adapted based on material or tissue type of the object.

4. The image processing system of claim 1, wherein the imaging apparatus is at least one of a full-field-of-view X-ray imaging apparatus and a slot-scanning X-ray imaging apparatus.

5. A method for processing an image, comprising:
    imaging an object;
    receiving dark-field image data obtained from the imaged object;
    performing a correction operation to correct said dark-field image data for Compton scatter to obtain Compton-Scatter corrected image data;
    estimating a Compton scatter estimate data based on the transmission image data in relation to said object;
    applying said Compton scatter estimate data to the dark-field image data or to underlying projection data from which the dark-field image data and/or transmission data have been constructed; and
    outputting the Compton scatter corrected image data.

6. The method of claim 5, wherein the Compton scatter estimate data is adapted based on material or tissue type of the object.

7. A non-transitory computer-readable medium having one or more executable instructions stored thereon which, when executed by at least one processor, cause the at least one processor to perform a method for processing an image, the method comprising:
    imaging an object;
    receiving dark-field image data obtained from the imaged object;
    performing a correction operation to correct said dark-field image data for Compton scatter to obtain Compton-Scatter corrected image data;
    estimating a Compton scatter estimate data based on the transmission image data in relation to said object;
    applying said Compton scatter estimate data to the dark-field image data or to underlying projection data from which the dark-field image data and/or transmission data have been constructed; and
    outputting the Compton scatter corrected image data.

* * * * *